US010334216B2

(12) United States Patent
Kamm et al.

(10) Patent No.: US 10,334,216 B2
(45) Date of Patent: Jun. 25, 2019

(54) IMAGING SYSTEM INCLUDING LENS WITH LONGITUDINAL CHROMATIC ABERRATION, ENDOSCOPE AND IMAGING METHOD

(71) Applicant: Sony CORPORATION, Tokyo (JP)

(72) Inventors: Markus Kamm, Stuttgart (DE); Paul Springer, Stuttgart (DE); Thimo Emmerich, Stuttgart (DE); Zoltan Facius, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 84 days.

(21) Appl. No.: 15/519,472

(22) PCT Filed: Aug. 11, 2015

(86) PCT No.: PCT/EP2015/068412
§ 371 (c)(1),
(2) Date: Apr. 14, 2017

(87) PCT Pub. No.: WO2016/071020
PCT Pub. Date: May 12, 2016

(65) Prior Publication Data
US 2017/0237960 A1 Aug. 17, 2017

(30) Foreign Application Priority Data

Nov. 6, 2014 (EP) ..................... 14003742

(51) Int. Cl.
*H04N 5/33* (2006.01)
*H04N 9/64* (2006.01)
(Continued)

(52) U.S. Cl.
CPC ........... *H04N 9/646* (2013.01); *H04N 5/2226* (2013.01); *H04N 5/2256* (2013.01); *H04N 5/332* (2013.01);
(Continued)

(58) Field of Classification Search
CPC ........ H04N 9/646; H04N 9/76; H04N 13/207; H04N 13/254; H04N 5/2256;
(Continued)

(56) References Cited

U.S. PATENT DOCUMENTS 6,241,656 B1   6/2001  Suga
7,724,977 B2*  5/2010  Liege ............... G06T 1/0007
                                                382/254
(Continued)

FOREIGN PATENT DOCUMENTS

JP    2014-206687 A    10/2014
WO    2012/095322 A1    7/2012

OTHER PUBLICATIONS

Lee et al, Optimal Illumination Stectrum for Endoscope (Year: 2011).*

(Continued)

*Primary Examiner* — Shan E Elahi
(74) *Attorney, Agent, or Firm* — Xsensus LLP

(57) ABSTRACT

An imaging system includes an optical unit that captures, from a scene, first images indifferent wavelength ranges when the scene is illuminated with not-structured light and second images of different wavelength ranges when the scene is illuminated with structured light. Thereby an imaging lens unit with longitudinal chromatic aberration is arranged between the scene and an imaging sensor unit. A depth processing unit may generate depth information on the basis of the second images by using optical triangulation. A sharpness processing unit uses the depth information to generate an output image by combining the first images. The optical unit of the imaging, system may be implemented in an endoscope.

21 Claims, 12 Drawing Sheets

(51) Int. Cl.
*H04N 9/04* (2006.01)
*H04N 5/222* (2006.01)
*H04N 13/257* (2018.01)
*H04N 13/207* (2018.01)
*H04N 13/254* (2018.01)
*H04N 5/225* (2006.01)
*H04N 9/083* (2006.01)
*H04N 9/76* (2006.01)

(52) U.S. Cl.
CPC ............. *H04N 9/045* (2013.01); *H04N 9/083* (2013.01); *H04N 9/76* (2013.01); *H04N 13/207* (2018.05); *H04N 13/254* (2018.05); *H04N 13/257* (2018.05); *H04N 2005/2255* (2013.01)

(58) Field of Classification Search
CPC ...... H04N 13/257; H04N 9/083; H04N 5/332; H04N 5/2226; H04N 9/045; H04N 2005/2255
USPC .......................................................... 348/46
See application file for complete search history.

(56) References Cited

U.S. PATENT DOCUMENTS

| | | | |
|---|---|---|---|
| 7,933,010 B2* | 4/2011 | Rahn | G01N 21/4795 356/213 |
| 8,369,579 B2 | 2/2013 | Frigerio | |
| 8,374,397 B2 | 2/2013 | Shpunt et al. | |
| 8,467,628 B2 | 6/2013 | Coffman | |
| 8,684,914 B2 | 4/2014 | McDowall et al. | |
| 2004/0174541 A1* | 9/2004 | Freifeld | G01B 11/024 356/614 |
| 2007/0103441 A1* | 5/2007 | Kong | G06F 3/0421 345/166 |
| 2009/0169095 A1* | 7/2009 | Zhuang | G01B 11/2545 382/154 |
| 2010/0053766 A1* | 3/2010 | Okada | G02B 15/177 359/686 |
| 2010/0284589 A1* | 11/2010 | Thiel | G01B 11/2518 382/128 |
| 2011/0057930 A1 | 3/2011 | Keller et al. | |
| 2011/0164323 A1* | 7/2011 | Liege | G02B 27/0075 359/618 |
| 2012/0182394 A1* | 7/2012 | Bae | H04N 13/0011 348/46 |
| 2013/0215404 A1* | 8/2013 | Den Boef | G01J 3/4412 355/44 |
| 2013/0217952 A1* | 8/2013 | Mawn | A61B 1/3132 600/8 |
| 2013/0278726 A1 | 10/2013 | Muhammad et al. | |
| 2014/0267007 A1* | 9/2014 | Capps | G06F 3/048 345/156 |
| 2014/0309495 A1* | 10/2014 | Kirma | G02B 23/243 600/109 |
| 2016/0270656 A1* | 9/2016 | Samec | A61B 3/085 |
| 2017/0109890 A1* | 4/2017 | Wang | H04N 5/2256 |
| 2017/0172662 A1* | 6/2017 | Panescu | A61B 90/37 |

OTHER PUBLICATIONS

Terry et al, An integrated port camera and display system for laparoscopy (Year: 2010).*

Chao-I Chen, et al., "Modeling Tumor/Polyp/Lesion Structure in 3D for Computer-Aided Diagnosis in Colonoscopy", SPIE Medical Imaging, International Society for Optics and Photonics, Total 8 Pages, (2010).

International Search Report and Written Opinion dated Oct. 28, 2015 in PCT/EP2015/068412 Filed Aug. 11, 2015.

* cited by examiner

IMAGING SYSTEM INCLUDING LENS WITH LONGITUDINAL CHROMATIC ABERRATION, ENDOSCOPE AND IMAGING METHOD

BACKGROUND

Field of the Disclosure

The present disclosure relates to an imaging system using depth information to exchange sharpness information among images of different wavelength ranges. The disclosure further relates to an endoscope as well as to an imaging method.

Description of Related Art

In digital imaging systems, optical systems capture light form 3D scenes and project the captured light onto a 2D image sensor arranged in an image plane. A depth of field within which high spatial frequencies can be obtained to get a sharp picture, depends, inter alia, on the physical dimensions of the optical system. Some applications for imaging systems, e.g., industrial endoscopes for non-destructive inspection of hollows such as combustion chambers or medical endoscopes for diagnostic and minimally invasive surgery image objects located in a very close distance to a lens system of the optical system at constricted physical dimensions as well as aperture and focal length of the optical system and have narrow depth of field.

There is a need for imaging systems combining small optical systems with high sharpness and large depth of field. The object of the present embodiments is achieved by the subject-matter of the independent claims. The dependent claims define further embodiments.

SUMMARY

The foregoing paragraphs have been provided by way of general introduction and are not intended to limit the scope of the following claims. The described embodiments, together with further advantages, will be best understood by reference to the following detailed description taken in conjunction with the accompanying drawings.

According to an embodiment an imaging system includes an optical unit configured to capture, from a scene, first images of different wavelength ranges when the scene is illuminated with not-structured light and second images of different wavelength ranges when the scene is illuminated with structured light, wherein an imaging lens unit with longitudinal chromatic aberration is arranged between the scene and an imaging sensor unit. A depth processing unit generates depth information. A sharpness processing unit uses depth information to generate an output image by combining the first images.

According to another embodiment an endoscope includes a tube portion and a tip portion attached at an end face of the tube portion. The tip portion includes an optical unit to capture, from a scene, first images of different wavelength ranges when the scene is illuminated with not-structured light, and second images of different wavelength ranges, when the scene is illuminated with structured light. An imaging lens unit with longitudinal chromatic aberration is arranged between the scene and an imaging sensor unit.

According to further embodiment an imaging method includes capturing, from a scene, first images of different wavelength ranges when the scene is illuminated with not-structured light, and second images of different wavelength ranges, when the scene is illuminated with structured light, wherein an imaging lens unit with longitudinal chromatic aberration is arranged between the scene and an imaging sensor unit. Depth information is generated on the basis of the second images. An output image is generated by using the depth information and combining the first images.

According to yet a further embodiment, an imaging system includes first means arranged in an equipment, e.g., a scanning equipment, for capturing, from a scene, first images of different wavelength ranges when the scene is illuminated with not-structured light, and second images of different wavelength ranges, when the scene is illuminated with structured light, wherein the first and second images are captured by using an imaging lens unit with longitudinal chromatic aberration. Second means generate depth information on the basis of the second images, wherein the second means are connected to the first means in terms of signal transmission. Third means obtain an output image by using the depth information, wherein the first images are combined. Third means are connected to the first and second means in terms of signal transmission.

BRIEF DESCRIPTION OF THE DRAWINGS

In the following drawings, like reference numerals designate identical or corresponding parts throughout the several views. The elements of the drawings are not necessarily to scale relative to each other. Features of the illustrated embodiments can be combined with each other to form yet further embodiments.

DESCRIPTION OF THE EMBODIMENTS

Figure 1:
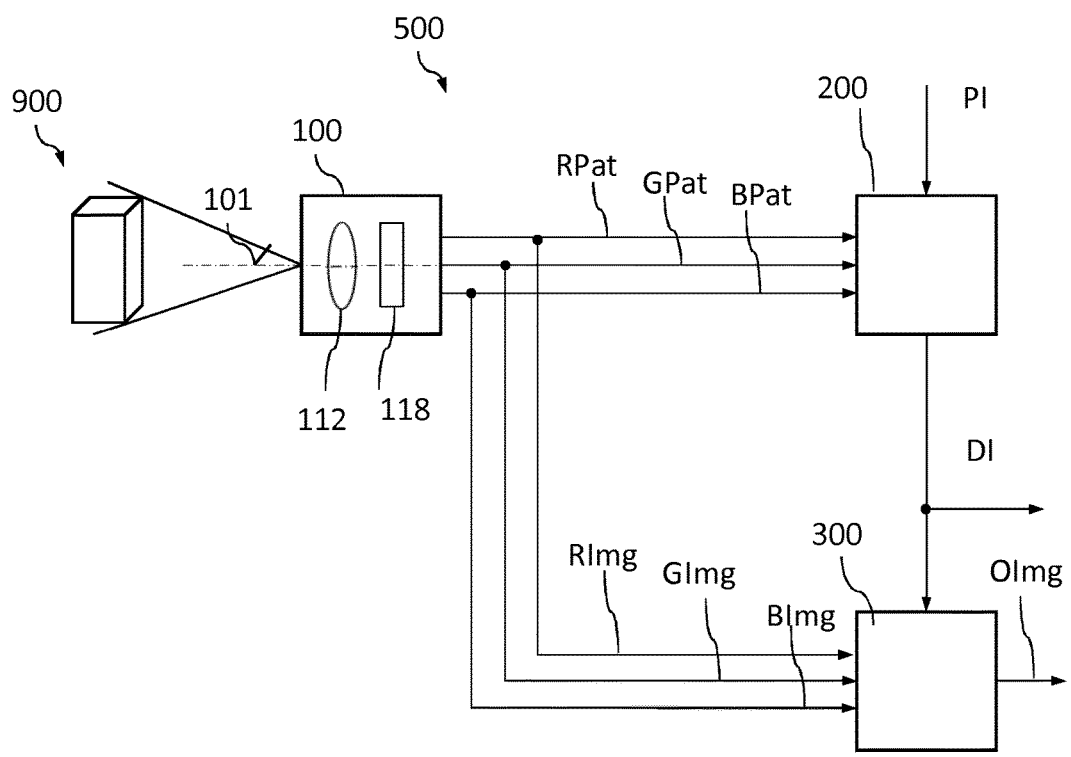
FIG. 1 is a schematic block diagram of an imaging system according to an embodiment.

FIG. 1 shows an imaging system 500 of an imaging apparatus, e.g. a camera, an industrial inspection system or a medical endoscope for diagnostic and/or minimally invasive surgery, e.g., a laparoscope. According to an embodiment, an aperture diameter of the imaging system is less than 5 mm, e.g., 3 mm. The imaging system 500 includes an optical unit 100 that captures two or more first images RImg, GImg, BImg assigned to different wavelength ranges when a scene 900 is completely illuminated with non-structured light. The optical unit 100 captures second images RPat, GPat, BPat of the same different wavelength ranges when the same scene 900 is illuminated with structured light. The optical unit 100 is controllable to capture the first images and the second images alternatingly. In the optical path 101 of the optical unit 100, an imaging lens unit 112 with longitudinal chromatic aberration is arranged between the scene 900 and an imaging sensor unit 118 that transforms the impinging light into electric signals or digital information representing the first and second images RImg, GImg, BImg, RPat, GPat, BPat.

A depth processing unit 200 receives the second images RPat, GPat, BPat obtained by illumination with structured light and further receives or holds pattern information PI descriptive for a shadow pattern applied during illumination of the scene 900 with the structured light. By applying optical triangulation the depth processing unit 200 gains depth information DI concerning picture details, objects, single pixels or pixel groups in the second images RPat, GPat, BPat. The depth processing unit 200 is a functional block, e.g., a software program, an electronic circuit or a combination of a software program and an electronic circuit, wherein the software program is a program code executed in a processor or controller.

A sharpness processing unit 300 receives the first images RImg, GImg, BImg as well as the depth information DI and may use the depth information DI to exchange sharpness information among the first images RImg, GImg, BImg in order to obtain improved versions of the first images RImg, GImg, BImg. The sharpness processing unit 300 further combines the improved versions of the first images RImg, GImg, BImg to generate an output image OImg, wherein the depth information DI may be used. The sharpness processing unit 300 is a functional block, e.g., a software program, an electronic circuit or a combination of a software program and an electronic circuit. The depth and sharpness processing units 200, 300 may be integrated in different integrated circuits or in the same integrated circuit.

For given dimensions of an optical unit, the imaging system 500 enhances image quality over a wide depth of field and avoids degradation of resolution, which usually is limited by the aperture-dependent blur. In addition, the imaging system 500 gains depth information DI which is nearly independent of the image content over the complete field of view. The depth information DI may be used to provide a user of the imaging apparatus with further information as regards the scene. For example, the depth information DI may be used for a 3D representation of the scene 900 on a monitor or display.

Figure 2A:
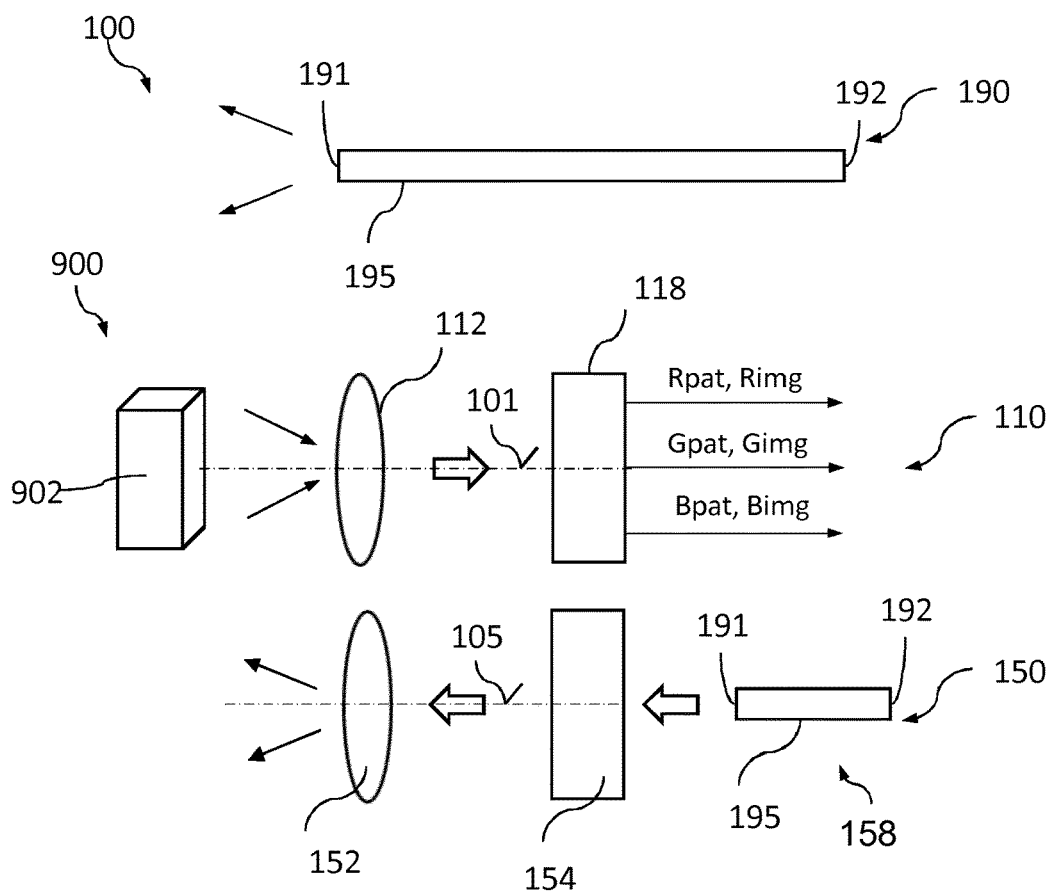
FIG. 2A is a schematic block diagram of an embodiment of an optical unit of the imaging system of FIG. 1.
Figure 2B:
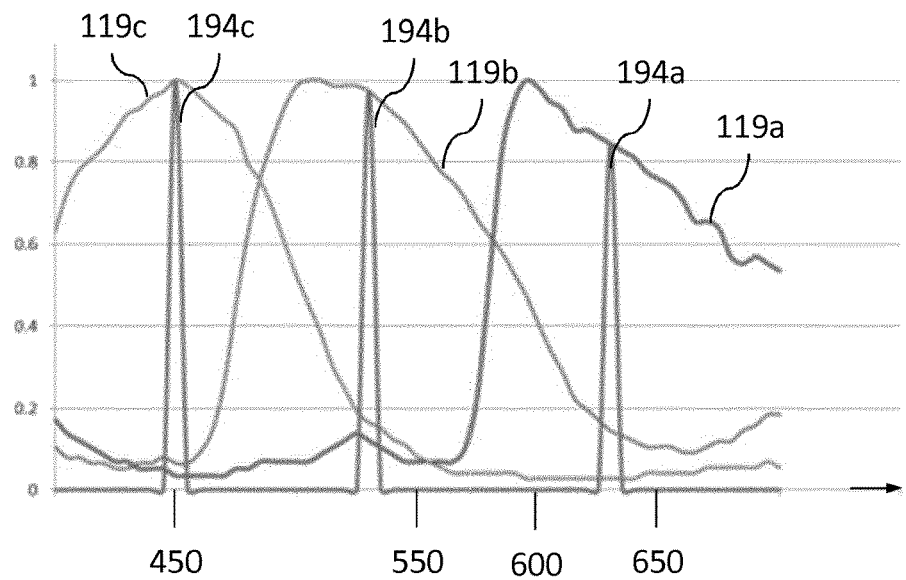
FIG. 2B is a schematic diagram of emission spectra of illumination units for discussing effects of embodiments concerning narrowband illumination.

FIGS. 2A and 2B refer to details of the optical unit 100. An illumination unit 190 completely illuminates the scene during capture of the first images RImg, GImg, BImg, wherein during capture of the first images RImg, GImg, BImg, the light illuminating the scene 900 is not structured. A projection unit 150 illuminates the scene during capture of the second images RPat, GPat, BPat with structured light. The illumination unit 190 and the projection unit 150 are alternatingly active. An imaging unit 110 includes the imaging lens unit 112 with longitudinal chromatic aberration and effective as a hyper-chromatic lens as well as the imaging sensor unit 118 that captures the first and second images RImg, GImg, BImg, RPat, GPat, BPat.

According to an embodiment, the illumination unit 190 includes one or more optical fibres 195 with exit face(s) 191 oriented to the scene 900 and junction face(s) 192 connectable to an external light source. During capture of the first images RImg, GImg, BImg, white light or a plurality of narrow wavelength ranges in a wavelength range containing visible light, UV (ultraviolet) radiation and IR (infrared) radiation is supplied through the optical fibres 195 to the scene 900.

According to another embodiment, the illumination unit 190 includes one or more active light sources such as LEDs (light emitting diodes) integrated in a housing encasing the optical unit 100. The light source may emit white light or a plurality of narrow wavelength ranges in a wavelength range containing the visible light, UV radiation and IR radiation.

The illumination unit 190 is arranged to illuminate the scene 900 with radiation at least in a wavelength range used by the imaging sensor unit 118. For example, if the imaging sensor unit 118 senses red, green and blue wavelength ranges, the illumination unit 190 illuminates the scene 900 in at least in the red, green and blue wavelength ranges, e.g., in a wavelength range from at least red light to at least blue light. If the imaging sensor unit 118 is sensitive to IR radiation, the illumination unit 190 illuminates the scene also in the IR band.

The projection unit 150 includes a projection illumination unit 158, a projection lens unit 152 arranged between the illuminated scene 900 and the projection illumination unit 158, and an optical element 154 in the optical path of the projection unit 150.

The projection illumination unit 158 may include one or more optical fibres 195 with exit face(s) 191 oriented to the scene 900 as well as junction face(s) 192 connectable to an external light source. According to another embodiment, the projection illumination unit 158 includes one or more active light sources such as LEDs integrated in a housing encasing the optical unit 100. The projection illumination unit 158 may emit radiation of the same spectral distribution as the illumination unit 190. According to a further embodiment, a common optical fibre, optical fibre bundle, or active light source is alternatingly effective as the illumination unit 190 and the projection illumination unit 158, e.g., by means of a switchable light gate or deflector.

The projecting lens unit 152 may be a lens system with longitudinal chromatic aberration. According to an embodiment, the projecting lens unit 152 shows the same longitudinal chromatic aberration characteristics as the imaging lens unit 112.

The optical element 154 in the optical path 105 between the projection illumination unit 158 and the illuminated scene 900 acts as a reticle having a grey-level pattern, which defines portions of the scene 900 which are at least partially shadowed, i.e., not fully illuminated during capture of the second images RPat, GPat, BPat.

The imaging lens unit 112 and the imaging sensor unit 118 of the imaging unit 110 are arranged along an optical axis 101 which is not identical with an optical axis 105 of the projection unit 150. The optical axes 101, 105 of the imaging unit 110 and the projection unit 150 may intersect with each other. According to another embodiment, the optical axes 101, 105 may be parallel to each other, wherein a distance between the optical axes 101, 105 is limited by the diameter of the optical unit 100 which limits the spacing between the imaging lens unit 112 and the projecting lens unit 152 such that this distance cannot exceed the diameter of the optical unit 100 itself. According to an embodiment, the distance between the optical axes 101, 105 is at most 2.5 mm.

According to an embodiment, the imaging and projection units 110, 150 have the same field of view and may be aligned to each other in a side-by-side or in a top-bottom arrangement. Both optical systems have a small intraocular distance less than 2.5 mm, e.g., in a range from 2 mm to 2.5 mm and the complete system dimensions may be comparable to current laparoscopic devices, by way of example.

The diagram of FIG. 2B refers to an embodiment using narrowband laser radiation for illuminating a scene with structured and not-structured light. For example, both the illumination unit 190 and the projection illumination unit 158 illuminate the scene with red, green and blue laser light 194a, 194b, 194c as illustrated in the diagram, which in addition shows the colour filter transmission characteristics 119a, 119b, 119c for red, green and blue colour filter sections 114a as illustrated in FIG. 3B. The use of quasi discrete wavelengths results in sharper first and second images since no wavelength dependent magnification can blur the first and second images.

Figure 3A:
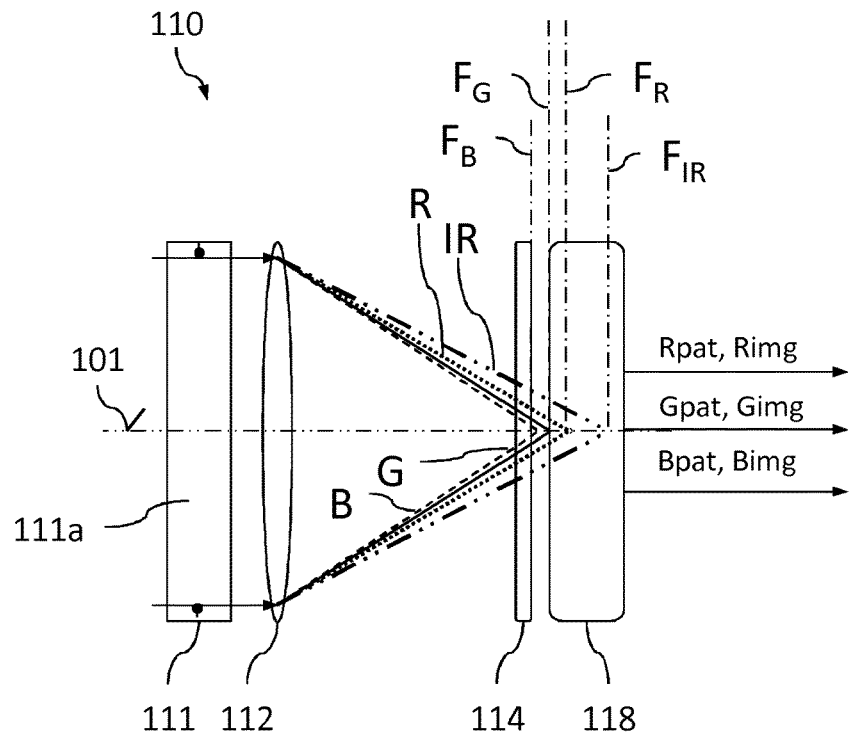
FIG. 3A is a schematic diagram showing details of an imaging unit of the optical unit in FIG. 2A according to an embodiment.
Figure 3B:
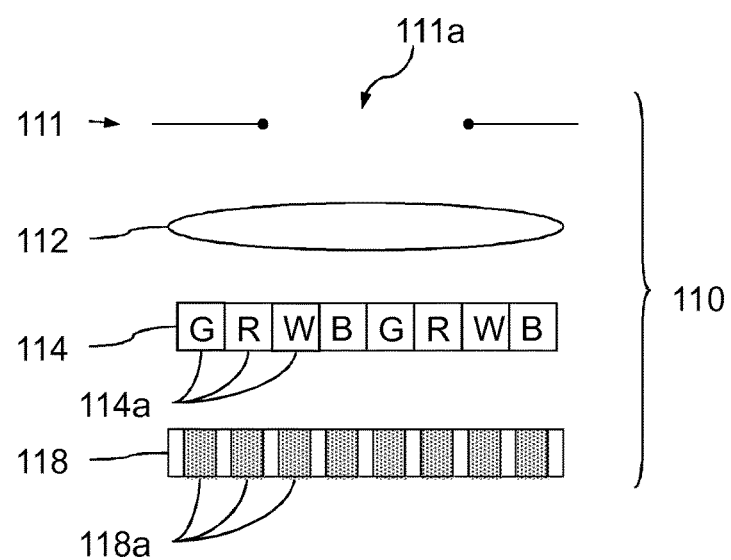
FIG. 3B is a schematic cross-section of the imaging unit of FIG. 3A.

FIGS. 3A and 3B show the imaging unit 110 in more detail. During capture of the scene, radiation that may contain visible light, UV radiation and IR radiation and that is descriptive for an image of the scene, passes through an aperture 111a of an aperture unit 111 as well as through the imaging lens unit 112 and incidents onto an imaging sensor unit 118. The size of the aperture 111a may be fixed or controllable.

The imaging lens unit 112 shows longitudinal chromatic aberration and may image, e.g., infrared radiation in a first focal plane FIR, visible red light in a focal plane FR, green light in a focal plane FG and blue light in a focal plane FB. The imaging lens unit 112 may be a micro-lens array including a plurality of segments, wherein each lens segment of the imaging lens unit 112 may be assigned to one single pixel sensor 118a of the imaging sensor unit 118 and to one colour filter section 114a of a colour filter unit 114.

According to an embodiment the imaging lens unit 112 may be a compound lens formed of a highly dispersive material like glass or plastics, where the index of refraction is a function of the wavelength of the incident light such that the focal length varies as a function of the wavelength. The imaging lens unit 112 may include compensation elements compensating for spherical and/or field dependent aberrations such that the imaging lens unit 112 exhibits no or only negligible spherical and field dependent aberrations. The imaging lens unit 112 may further be designed to compensate for different magnification ratios in the different focal planes.

Due to the longitudinal chromatic aberration of the imaging lens unit 152, the colour images blue, green, red and infrared focus at different distances from near to far. By exchanging sharpness among the colour images, a working range of the imaging unit 110 is expanded. In the following, sub-ranges of the visible spectrum as well as wavelength ranges next to the visible spectrum such as IR and UV are referred to as 'colour', irrespective of whether or not the wavelength range is perceptible by the human eye. For example, a 'colour filter' may also be a filter letting pass only radiation in the IR or UV spectral range.

The imaging sensor unit 118 includes a plurality of pixel sensors 118a, wherein each pixel sensor 118a contains a photo sensor that converts a photo signal from the incident light into an electronic signal. The pixel sensors 118a may be formed in a semiconductor substrate in one plane or in different planes. A pitch (center-to-center) distance of the pixel sensors may be in a range from 0.5 µm to 2 µm. According to an embodiment the imaging sensor unit 118 may be an HD (high definition) image sensor with about 2 MP resolution.

For example, the imaging sensor unit 118 may have a vertically integrated photodiode structure with deep photodiodes formed in a substrate section a few microns beneath surface photodiodes, which are formed along a substrate surface of a semiconductor substrate. Visible light is absorbed in the surface section of the semiconductor substrate, whereas infrared radiation penetrates deeper into the semiconductor substrate. As a result, the deep photodiodes receive infrared radiation only. According to another embodiment the imaging sensor unit 118 may have a lateral integrated photodiode structure with the photodiodes arranged in an array.

A colour filter unit 114 may be arranged between the imaging lens unit 112 and the imaging sensor unit 118 or between the aperture unit 111 and the imaging lens unit 112. The colour filter unit 114 may be arranged in close contact to the imaging sensor unit 118 and may include a plurality of colour filter sections 114a, wherein each colour filter section 114a has a filter colour, for example green, red, blue, magenta, yellow, white, IR, or UV.

Each colour filter section 114a may be assigned to one single pixel sensor 118a such that each pixel sensor 118a receives colour-specific image information. For example, the colour filter sections 114a may be arranged matrix-like in columns and rows. Colour filter sections 114a assigned to different filter colours may alternate along the row direction and the column direction in a regular manner. For example, each group of four colour filter sections 114a forming a 2×2 matrix may form a Bayer mosaic pattern, wherein colour filter sections 114a with the filter colour "green" are arranged on a first diagonal of the 2×2 matrix, and one colour filter section 114a with a filter colour "red" and one colour filter section 114a with the filter colour "blue" are arranged on the other diagonal of the 2×2 matrix. With the Bayer mosaic pattern, the sampling rate for the filter colour "green" is twice that of the filter colours "red" and "blue" to take into account that the colour green carries most of the luminance information for the human eye.

According to another embodiment, the colour filter sections 114a may be arranged to form an RGBE-mosaic pattern with "Emerald" as a fourth filter colour, a CYYM mosaic pattern with one cyan, two yellow and one magenta colour filter sections 114a or a CYGM mosaic pattern with one cyan, one yellow, one green and one magenta colour filter sections 114a arranged in 2×2 unit matrices, which are repeatedly arranged within the colour filter unit 114. According to another embodiment, the colour filter unit 114 includes a mosaic of unit matrices with three colour filter sections of three different filter colours and one transparent filter section without colour filtering properties and transparent for all colours within the visible spectrum. The transparent and the colour filter sections 114a may be arranged to form an RGBW mosaic pattern, for example a 4×4 or a 2×4 RGBW mosaic pattern, by way of example.

In accordance with an embodiment, the colour filter 114 contains at least one colour filter section type being transparent for IR or UV radiation. For example, the colour filter 114 is an RGBIR filter with each 2×2 unit matrix containing one red, one green, one blue and one infrared colour filter section 114a and with the unit matrices regularly arranged to form a mosaic pattern. The four colours R, G, B and IR can be arranged by any permutation within the 2×2 unit matrices.

The IR and/or UV radiation may pass the colour filter unit 114 in filter sections 114a transparent for IR radiation or UV radiation between the colour filter sections 114a. According to other embodiments the colour filter unit 114 does not include sections assigned to the deep photodiodes, since the colour filter sections 114a may be transparent for a portion of the frequency range of infrared radiation.

Figure 4A:
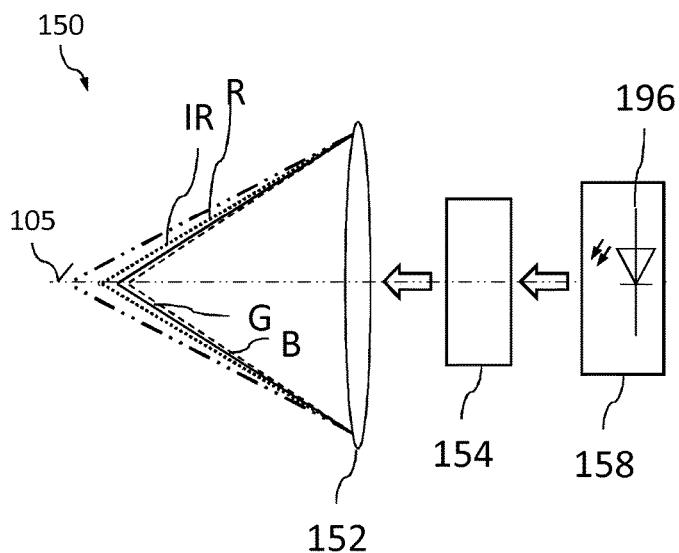
FIG. 4A is a schematic diagram showing details of a projecting unit of the optical unit in FIG. 2A according to an embodiment.

FIG. 4A shows a projection unit 150 with a projecting lens unit 152 and an optical element 154 arranged between a projection illumination unit 158 and the projecting lens unit 152. According to the illustrated embodiment, the projection illumination unit 158 is an active light source 196, e.g., an LED or an LED array. The projecting lens unit 152 may have the same optical performance as the imaging lens unit 112 including the same longitudinal chromatic aberration. With a hyper chromatic projection lens unit 152 the structured light pattern can be detected and processed more reliably as it is sharp in at least one color channel. In addition, a hyper chromatic projection lens unit 152 may inversely compensate the lateral chromatic aberration and distortion of the imaging lens unit 112.

Figure 4B:
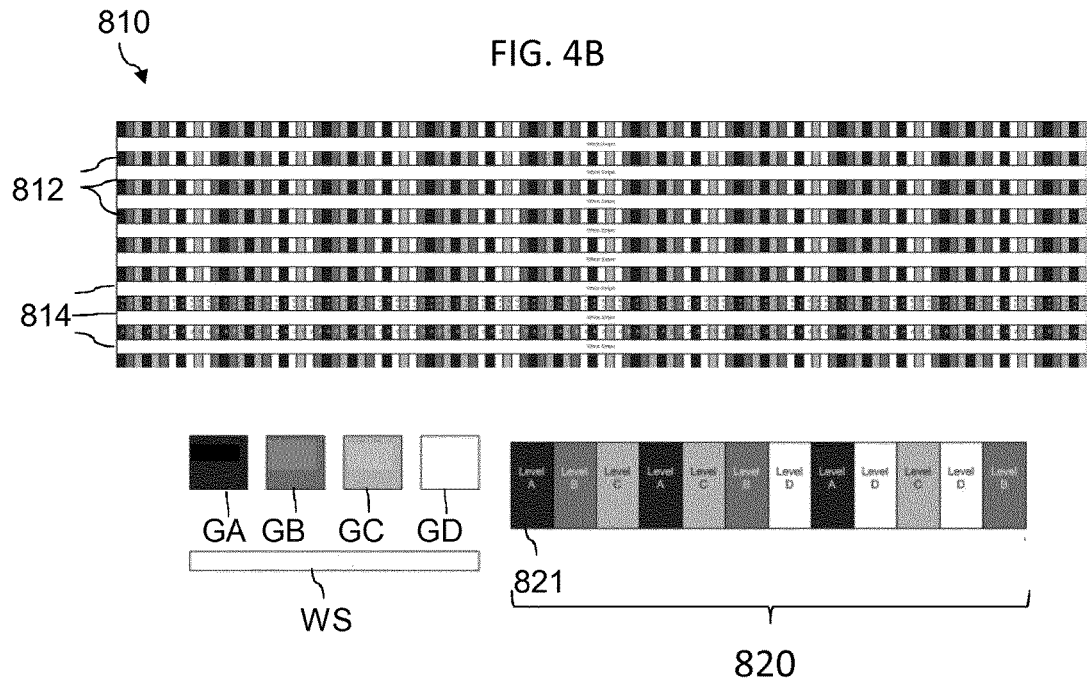
FIG. 4B is a schematic plan view of an optical element of the projecting unit in FIG. 4A and shows a shadow pattern according to an embodiment.

FIG. 4B shows details of the optical element 154 in FIG. 4A. The optical element 154 may be a micro-structured reticle with a shadow pattern that may be imprinted on a surface of the reticle. The shadow pattern includes not-shadowing (white) portions and shadowing portions, the latter either totally shadowing (black) or partially shadowing (greyscale). According to an embodiment, the greyscale or grey level of the shadowing portions may be coded to avoid ambiguities in the mapping between the original pattern and the projected pattern. For example, four different greyscale levels may code twelve different sorts of edges in the structured light pattern resulting from projecting the shadow pattern of the optical element 154 on the imaged object.

The partially shadowing portions may form a 1D pattern, e.g. a stripe pattern with variations along one direction, or a 2D pattern, e.g., a dot pattern or a grid with variations along two orthogonal directions. The shadow pattern may be a Gray-coded composite pattern to reduce possible ambiguities during structured light pattern recovering.

In shadow pattern 810 illustrated in FIG. 4B includes patterned horizontal lines 812 which may be separated by white lines 814 having the grey level white WS. The horizontal lines include a repetitive pattern 820 that may include twelve fields 821 of four different grey levels GA, GB, GC, GD between black and white such that the shadow pattern in total includes five different grey levels.

When projected onto the scene 900, the different distances of objects in the scene 900 distort the projected structured light pattern for an observer distant to the optical axis 105 of the projection unit 150. By comparing corresponding points in the projected structured light pattern and the imprinted shadow pattern described by pattern information PI, depth information DI can be derived from the second images RPat, GPat, BPat at least for pixels on edges of the structured light pattern.

Figure 5A:
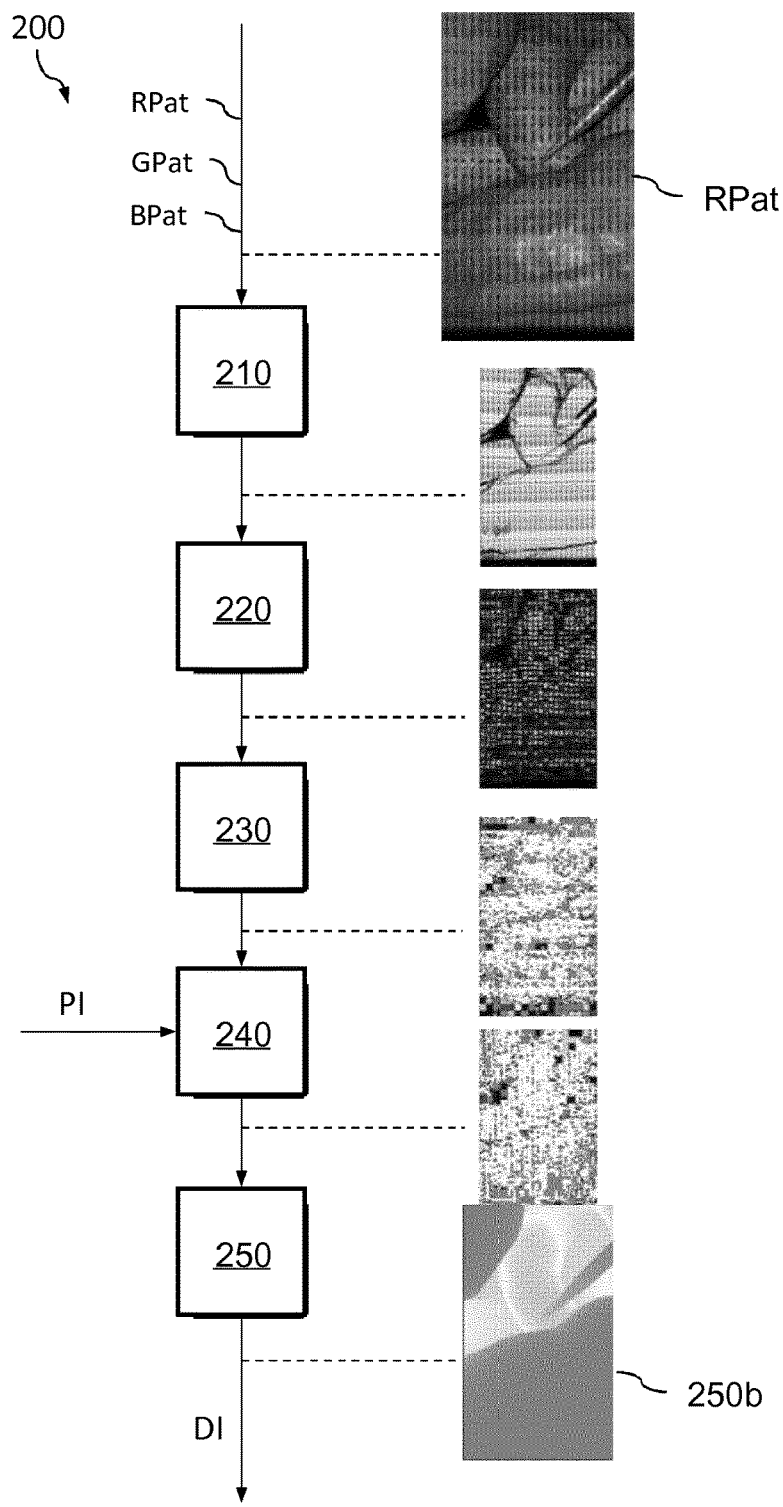
FIG. 5A is a schematic block diagram illustrating functional blocks of the depth processing unit in FIG. 1 according to an embodiment.

FIG. 5A illustrates functional blocks of the depth processing unit 200 as well as a process of depth sensing, which may be performed by the depth processing unit 200. Each of the functional blocks 210, 220, 230, 240, 250 may correspond to an electronic circuit, e.g. an integrated circuit, an FPGA (field programmable gate array), an ASICs (application specific integrated circuit) or a DSP (digital signal processor), or to a program routine that may be executed in a digital signal processor or to a combination of both.

A first functional block 210 of the depth processing unit 200 receives the second images obtained by the optical unit 100 during illumination of a scene with structured light, inter alia, for example an image RPat captured in the red wavelength range and containing the projected shadow pattern. The structured light may be structured white light or structured light of at least two separated narrow wavelength ranges in a spectral range including IR radiation, visible light and UV radiation.

The first functional block 210 may use white light information to gain a scaling factor for recovering the projected shadow pattern in the second images RPat, GPat, BPat in order to increase accuracy and robustness of the depth estimation. According to an embodiment based on a 2D shadow pattern and exclusively using spatial information, the scaling factor is determined from the white (not-shadowed) portions of the current second images RPat, GPat, BPat.

Figure 5B:
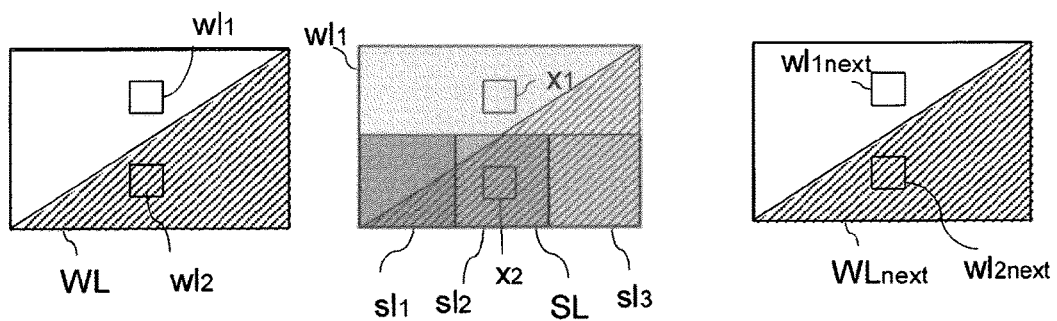
FIG. 5B is a schematic diagram for illustrating the effect of a scaling factor used in the depth processing unit in FIG. 5A.

FIG. 5B shows calculation and use of a scaling factor sf for a no motion case by using pixel values wI1, wI2 in a first image WL obtained by illumination with not-structured light, corresponding pixel values x1, x2 in a second image SL obtained by illumination with structured light with fields of grey levels sI1, sI2, sI3 and corresponding pixel values wI1nxt, wI2nxt in a subsequent image WLnxt obtained by illumination with not-structured light.

The scaling factor sf may be obtained by warping the pixel values observed in the temporal adjacent images obtained by illumination with not-structured light and forming the reciprocal value of the result of the warping. According to an embodiment, the scaling factor sf(x1) may be 255/((wI1+wI1nxt)/2).

The scaling factor sf is multiplied with the corresponding pixel value x1, x2 in the image obtained by illumination with structured light to obtain a compensated version of the image obtained by illumination with the structured light. In this way, the scaling factor sf can be used to recover the structured light pattern from the images obtained by illumination with structured light, which contain scene information illuminated by the structured light.

According to another embodiment based on a 1D or 2D shadow pattern and using motion-adaptive spatio-temporal information, the first functional block 210 obtains the scaling factor from the current second images RPat, GPat, BPat as well as the preceding and/or the subsequent first images RImg, GImg, BImg obtained by illumination with non-structured light. According to a further embodiment based on a 1D or 2D shadow pattern and using motion-compensated spatio-temporal information, the first functional block 210 obtains the scaling factor from current second images RPat, GPat, BPat as well as motion compensated versions of the preceding and/or the subsequent first images RImg, GImg, BImg.

A second functional block 220 determines pixels or pixel groups (depth points) suitable for depth estimation in the current second images RPat, GPat, BPat. According to an embodiment the second functional block 220 detects edge positions with sub-pixel accuracy and selects pixels or pixel groups at edges of the detected stripe pattern as depth points.

Based on the greyscale values of adjacent stripes a third functional block 230 may assign labels to the depth points.

A fourth functional block 240 applies optical triangulation on the labeled depth points in the second images RPat, GPat, BPat and their counterparts in the undistorted shadow pattern described by the pattern information PI in order to determine the depth values for the depth points. According to an embodiment, the fourth functional block 240 further assesses the quality of each triangulation result by measuring the reliability using the scaling factor and a measure for the sharpness at the respective depth point in order to reduce errors in the triangulation results. For example, the pertinent measure of sharpness at the respective depth point is the edge width, which is the width of an edge that defines the respective label. It is a per color channel derived parameter.

A fifth functional block 250 uses a depth propagation algorithm for obtaining depth values for pixels or pixel groups between the depth points and outputs depth information DI that may be or contain a dense depth map 250b assigning depth values to each pixel in the second images RPat, GPat, BPat. The results can be obtained in real time for frame rates of at least 30 Hz such that the results may be applied to the subsequently captured first images. In FIG. 5A, the depth values of the depth map 250b are colour-coded for illustrative purpose.

Figure 6:
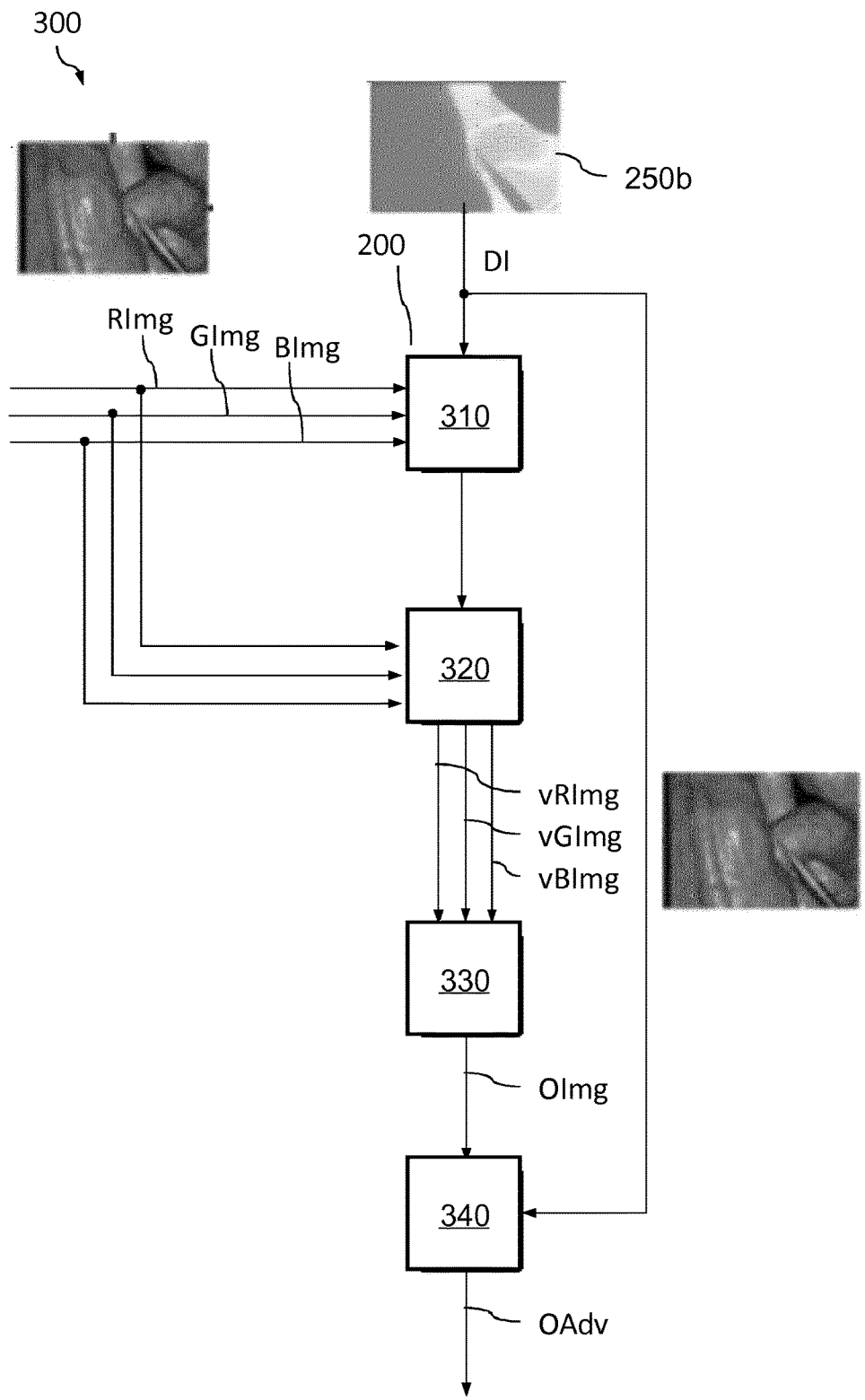
FIG. 6 is a schematic block diagram illustrating functional blocks of the sharpness processing unit in FIG. 1 according to an embodiment.

FIG. 6 illustrates functional blocks of the sharpness processing unit 300 as well as a process of sharpness transfer, which may be performed by the sharpness processing unit 300. Again, each of the functional blocks 310, 320 may correspond to an electronic circuit, e.g., an integrated circuit such as an FPGA, an ASIC or a DSP, or to a program routine executed in an electronic circuit, e.g., a DSP or to a combination of both.

A first functional block 310 of the sharpness processing unit 300 may compare, for single pixels, pixel groups and/or objects in the first images RImg, GImg, BImg values descriptive for sharpness in the respective image portion, e.g., a content of high spatial frequencies and identifies, by using the depth information DI, the one which contains the sharpest information about the concerned single pixel, pixel group or object.

A second functional block 320 may transport the sharpness information from that first image carrying the highest spatial frequencies in the region of interest to the other first images RImg, GImg, BImg to obtain improved versions vRImg, vGImg, vBImg of the first images, wherein second functional block 320 may use the depth information DI to identify the sharpest channel and to copy high spatial frequencies of the sharpest one of the first images RImg, GImg, BImg for the respective image region to the other first images RImg, GImg, BImg. For example, to each blurred sub-region of one of the first images RImg, GImg, BImg a high-pass filtered version of the sharpest first image RImg, GImg, BImg for the respective sub-region may be added or superposed. The strength of the high-pass maybe set according to an actual depth since a-priori-knowledge exists about the lens characteristics.

A third functional block 330 combines the improved first images to obtain a nearly all-in-focus output image OImg, which may be a colour or greyscale image. According to an embodiment, a fourth functional block 340 may further combine the output image OImg with the depth information DI to generate an improved output image OAdv visualizing a depth information for each pixel, e.g., by a colour coded 2D representation or a 3D representation.

The output image OImg or the improved output image OAdv may be stored in a non-volatile memory of the imaging system, for example as a set of digital values representing a greyscale or colour image. Alternatively or in addition, the output images OImg or the improved output images OAdv may be displayed on a display device of the imaging system, may be output to another system connected to the imaging system through a wired or wireless communication channel, or may be supplied to a processing system or application for processing further the information contained in the output images OImg.

Figure 7:
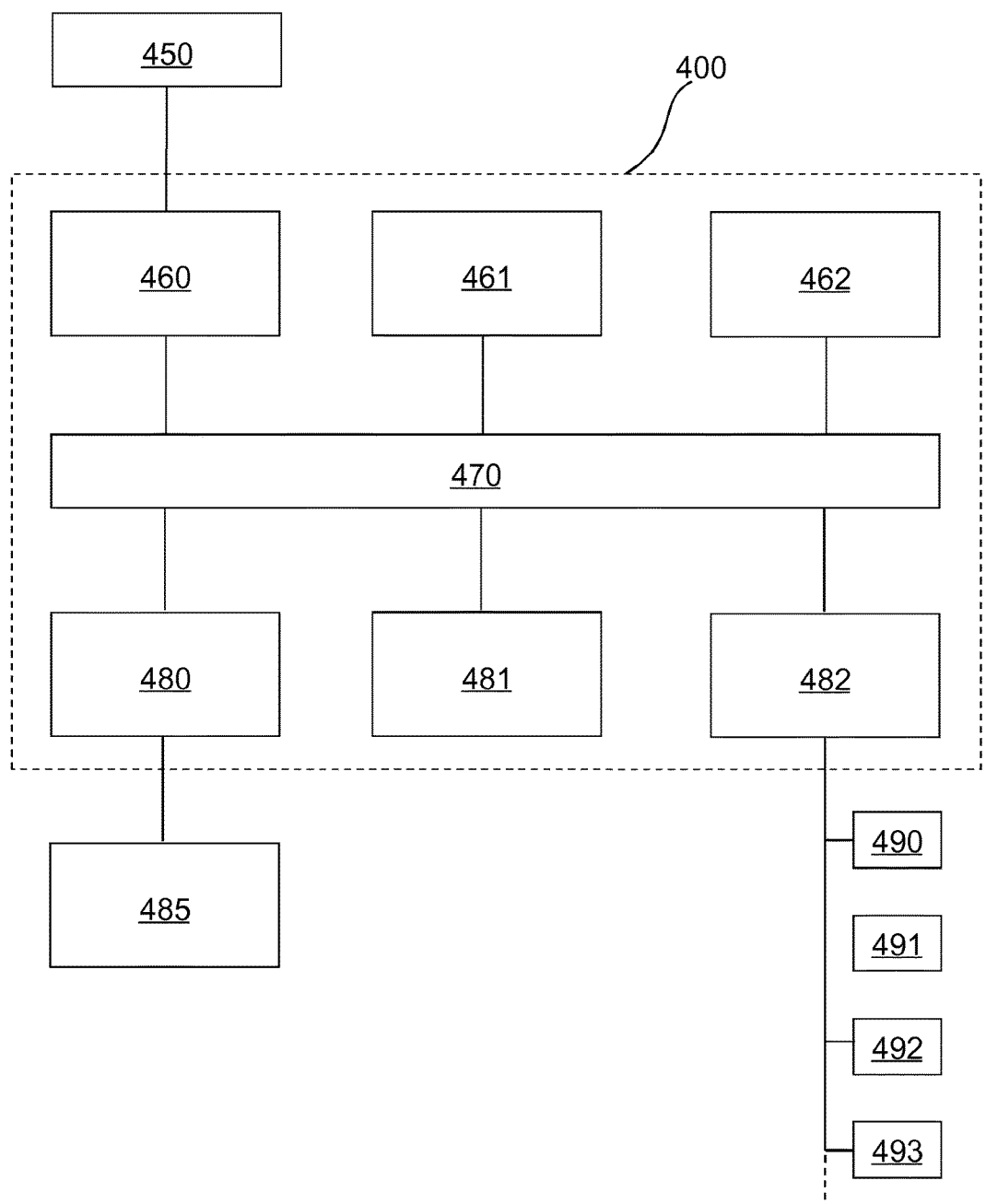
FIG. 7 is a schematic functional block diagram of a processor system according to a further embodiment.

FIG. 7 is a block diagram of a processing system 400 embodying aspects of this disclosure including aspects involving a computer generating an output image on the basis of images obtained by an optical unit including a hyper-chromatic lens unit. The processes, algorithms and electronically driven systems described herein can be implemented via a discrete control device or computing system consistent with the processing system 400.

The processing system 400 can be implemented using a microprocessor or its equivalent, such as a central processing unit 481 (CPU) or at least one application specific processor ASP. The microprocessor utilizes a computer readable storage medium, such as a memory 461 (e.g., ROM, EPROM, EEPROM, flash memory, static memory, DRAM, SDRAM, and their equivalents), that control the microprocessor to perform and/or control the imaging method. Other storage mediums can be controlled via a controller, such as a disk controller 462, which controls a hard disk drive or optical disk drive. A central bus system 470 may connect components of the processing system 400 with each other and provides at least one path for digital communication between them.

A video controller 460 may image the output image or may use the depth information to render a 3D image that can be displayed on a monitor 450. The video controller 460 may include a graphic processing unit for improved computational efficiency. Additionally, an I/O (input/output) interface 482 may receive input data from a keyboard 490 or a pointing device 491 for controlling parameters of the various processes and algorithms of this disclosure or for controlling display characteristics. The monitor 450 may include a touch-sensitive interface to a command/instruction interface. Other peripherals can be incorporated, including a scanner or a web cam when image-based data entry is used.

The components of the processing system 400 may be coupled to a network 485, such as the Internet or a local intranet, via a network interface 480 for the transmission or reception of data, including controllable parameters. The network 485 may provide a communication path to a mobile device, which can be provided by way of packets of data.

According to an embodiment the processing system 400 may receive the first and second images from the optical unit may through the I/O interface 482. According to another embodiment, the processing system 400 may receive the first and second images from the optical unit through the network interface 480.

Figure 8:
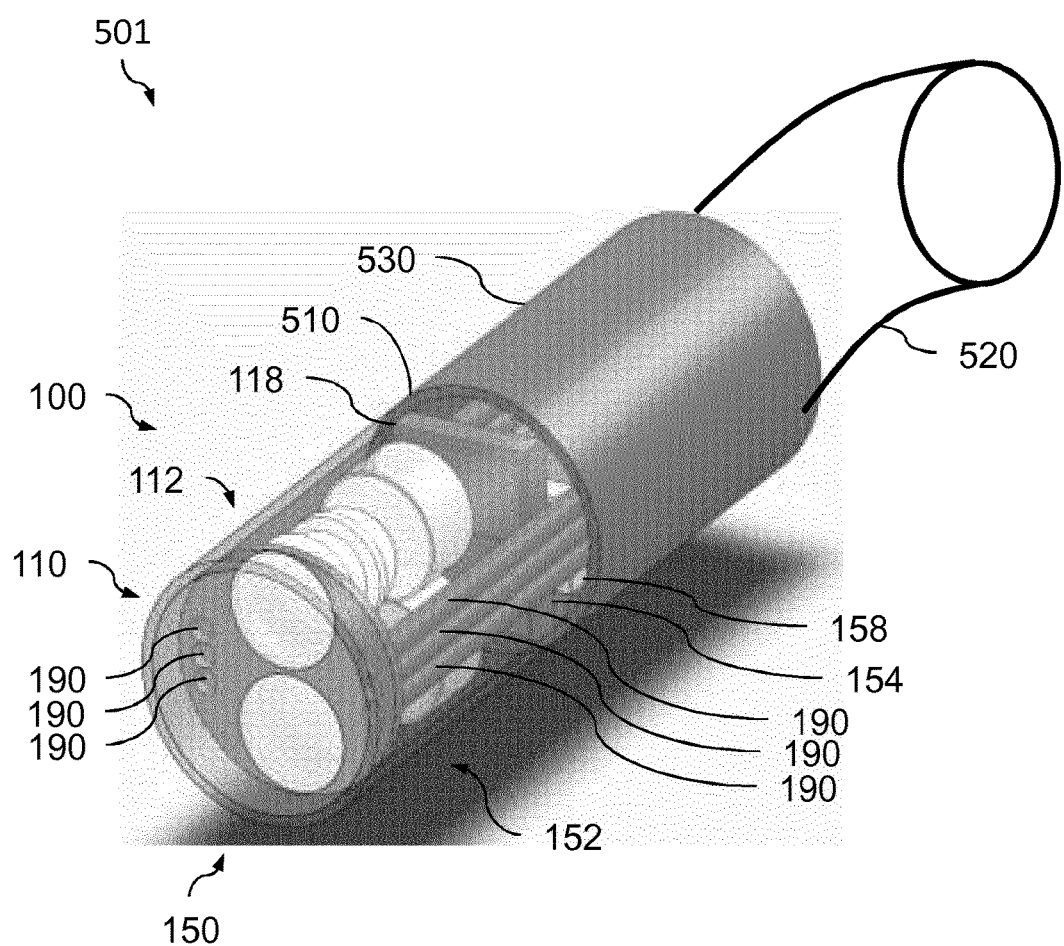
FIG. 8 is a schematic perspective view of an endoscope according to a further embodiment.

FIG. 8 shows a portion of a scanning equipment such as an endoscope 501 that may be used in industrial applications, for diagnostics or for minimally invasive surgery, by way of example. A cylindrical tip portion 510 is attached to an end face of a rigid or flexible tube portion 520 that may include optical fibers and electrical wirings. The tip portion 510 includes an optical unit 100 as described in detail in the forgoing. A housing 530 with a transparent front surface and an opaque cylinder surface may encapsulate the optical unit 100.

The optical unit 100 captures first images of different wavelength ranges from a scene when the scene is completely illuminated. The optical unit 100 further captures second images of different wavelength ranges from the scene when the scene is illuminated with structured light. The imaging unit 110 with the imaging sensor unit 118 is arranged in a first half cylinder of the tip portion 510 and the projection unit 150 with the optical element 154 including the shadow pattern in a second half cylinder.

A diameter of the tip portion 510 may be in a range from 3 mm to 5 mm. An aperture of the imaging unit 110 may be F/4 or smaller. The endoscope 501 may image scenes at a working range from 20 mm to 200 mm without sharpness degradation.

Figure 9:
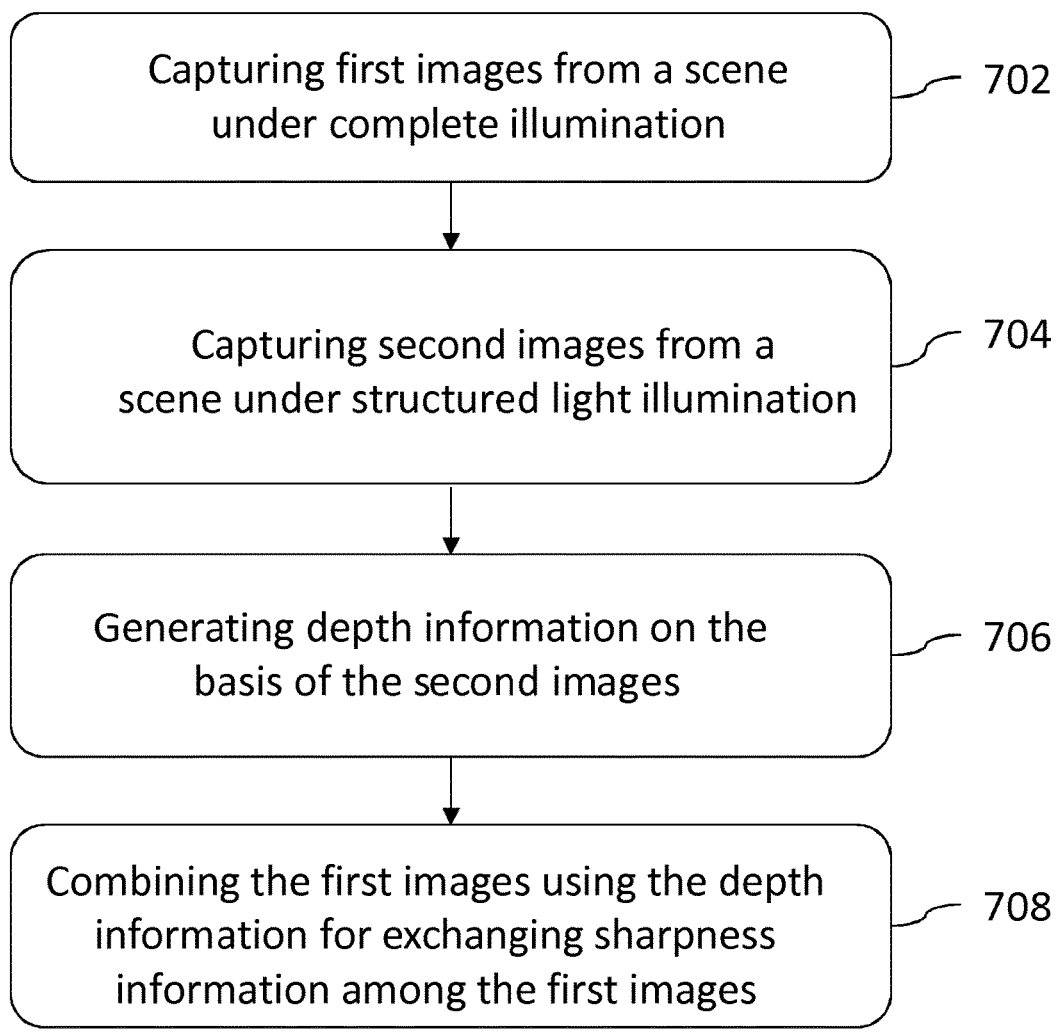
FIG. 9 is a simplified flowchart of an imaging method according to a further embodiment.

FIG. 9 illustrates an imaging method. First images of different wavelength ranges are captured, by using a hyperchromatic imaging lens unit, when a scene is completely illuminated (702). Second images of the same different wavelength ranges are captured when the scene is illuminated with structured light, wherein the same hyper-chromatic imaging lens unit is used (704). On the basis of the second images, depth information is obtained by using optical triangulation of image portions identified by a shadow pattern of the structured light (706). Using the obtained depth information, an output image is generated by combining the first images after exchanging sharpness information among the first images (708).

Figure 10A:
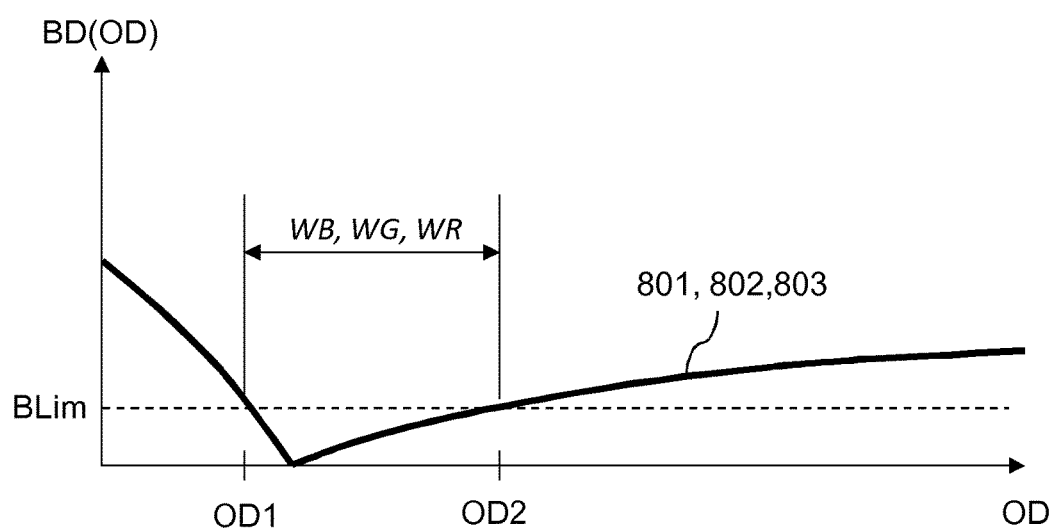
FIG. 10A is a diagram plotting the blur functions of color channels of a lens with corrected chromatic aberration for discussing effects of the embodiments.
Figure 10B:
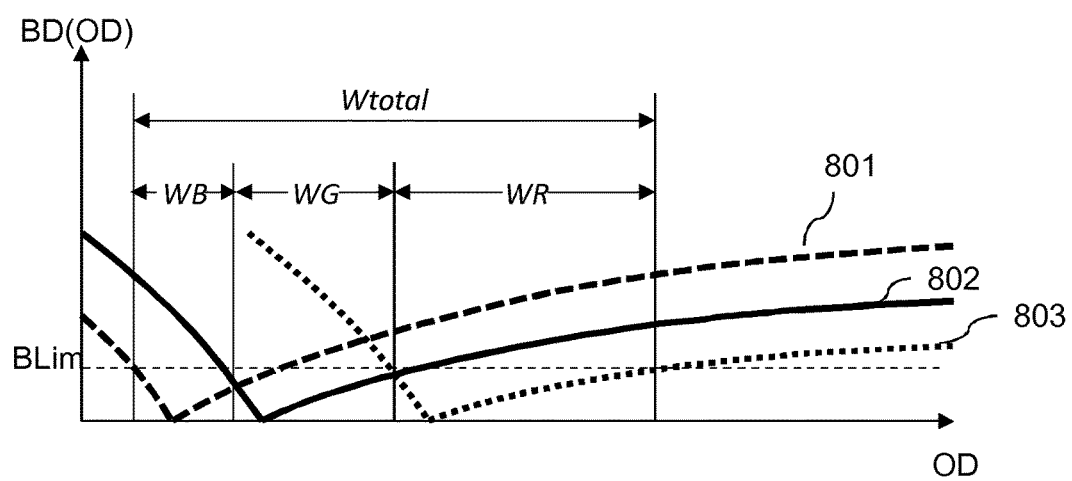
FIG. 10B is a diagram plotting the blur functions of color channels of a hyper chromatic lens for discussing effects of the embodiments.

FIGS. 10A and 10B illustrate the expansion of the working range by use of a hyper chromatic lens by diagrams plotting a blur diameter BD as a function of an object distance OD. A blur diameter BLim indicates the acceptable blur diameter and sets the limits OD1, OD2 of the working ranges for the blue, green and red blur functions 801, 802, 803.

In FIG. 10A, the chromatic aberration of a lens is perfectly corrected such that all colors of interest focus in the same plane. The blur functions 801, 802, 803 for blue, green and red coincide and their working ranges WB, WG, WR overlap with each other.

In FIG. 10B, the longitudinal chromatic aberration of a lens is not corrected or even more pronounced than in a not corrected lens such that the colors focus in different planes and the concerned color blur functions 801, 802, 803 as well as their working ranges WB, WG, WR are shifted to each other. For example, the working range WB of the blue channel is shifted to shorter distances whereas the working range WR of the red channel is shifted to longer distances. The working ranges WB, WG, WR of the colors of interest concatenate and by exchanging the sharpness among all color channels an expanded total working range Wtotal can be achieved.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the disclosure, as well as other claims. The disclosure, including any readily discernible variants of the teachings herein, defines, in part, the scope of the foregoing claim terminology.

The present technology can also be configured as described below.

(1) An imaging system comprising:
an optical unit configured to capture, from a scene, first images in different wavelength ranges when the scene is illuminated with not-structured light, and second images of different wavelength ranges when the scene is illuminated with structured light, wherein an imaging lens unit with longitudinal chromatic aberration is arranged between the scene and an imaging sensor unit;
a depth processing unit configured to generate depth information on the basis of the second images; and
a sharpness processing unit configured to generate an output image based on the depth information and the first images.

(2) The imaging system according to (1), wherein
the optical unit comprises a projection unit configured to illuminate the scene with structured light, the projection unit comprising a controllable projection illumination unit and a projection lens unit with longitudinal chromatic aberration arranged between the projection light source and the scene.

(3) The imaging system according to (2), wherein
optical axes of the imaging unit and the projection unit are parallel to each other.

(4) The imaging system according to any one of (1) to (3), wherein
the sharpness processing unit is configured to generate the output image based on the first images after exchanging sharpness information among the first images.

(5) The imaging system according to (4), wherein
the imaging lens unit and the projection lens unit have the same longitudinal chromatic aberration.

(6) The imaging system according to any one of (2) to (3), wherein
the projection unit comprises an optical element including transparent and at least partially opaque features forming a shadow pattern.

(7) The imaging system according to (6), wherein
the shadow pattern is a greyscale coded pattern.

(8) The imaging system according to any one of (1) to (7), wherein
the optical unit is configured to capture the first images and the second images alternately.

(9) The imaging system according to any one of (1) to (8), further comprising
an illumination unit configured to illuminate the scene with non-structured light during capturing of the first images.

(10) The imaging system according to (9), wherein
the illumination unit comprises one or more optical fibers with exit faces oriented to the scene and junction faces connectable to an external light source.

(11) The imaging system according to any one of (9) or (10), wherein
the illumination unit is configured to illuminate the scene with a broadband emission spectrum covering at least the spectral range of visible light.

(12) The imaging system according to any one of (9) or (10), wherein
the illumination unit is configured to illuminate the scene with two or more separated narrowband emission spectra.

(13) The imaging system according to any one of (1) to (12), wherein
the depth processing unit is configured to generate the depth information from the second images by optical triangulation.

(14) The imaging system according to any one of (1) to (13), wherein
the sharpness processing unit is configured to obtain spatial frequency distributions of the first images as sharpness information, to extract high frequency components of the spatial frequency distributions from at least one of the first images, to add the extracted high frequency components to the remaining first images to generate corrected first images, and to generate the output image by combining the corrected first images using the depth information.

(15) An endoscope system comprising the imaging system according to any one of (1) to (14).

(16) An endoscope comprising:
   a tube portion; and
   a tip portion attached at an end face of the tube portion and comprising an optical unit configured to capture, from a scene, first images of different wavelength ranges when the scene is illuminated with not-structured light and second images of different wavelength ranges when the scene is illuminated with structured light, wherein an imaging lens unit with longitudinal chromatic aberration is arranged between the scene and an imaging sensor unit.

(17) The endoscope according to (16), further comprising
   an illumination unit configured to illuminate the scene during capturing of the first images.

(18) The endoscope according to any one of (16) or (17), wherein
   the optical unit comprises a projection unit configured to illuminate the scene with structured light, the projection unit comprising a controllable projection illumination unit and a projection lens unit with longitudinal chromatic aberration arranged between the projection illumination unit and the scene.

(19) An imaging method comprising:
   capturing, from a scene, first images of different wavelength ranges when the scene is illuminated with not-structured light and second images of different wavelength ranges when the scene is illuminated with structured light, wherein an imaging lens unit with longitudinal chromatic aberration is arranged between the scene and an imaging sensor unit;
   generating depth information on the basis of the second images; and
   generating, by using the depth information, an output image by combining the first images.

(20) The imaging method according to (19), wherein
   depth information is generated by using optical triangulation of image portions identified by a shadow pattern of the structured light.

(21) An imaging system comprising:
   first means arranged in an equipment for capturing, from a scene, first images of different wavelength ranges when the scene is illuminated with not-structured light and second images of different wavelength ranges when the scene is illuminated with structured light, wherein the first and second images are captured by using an imaging lens unit with longitudinal chromatic aberration;
   second means for generating depth information on the basis of the second images, wherein the second means are connected to the first means in terms of signal transmission, and
   third means for generating, by using the depth information, an output image by combining the first images, and wherein the third means are connected to the first and second means in terms of signal transmission.

The invention claimed is:

1. An imaging system comprising:
   an optical unit to capture, from a scene, first images in different wavelength ranges when the scene is illuminated with non-structured light, and second images of different wavelength ranges when the scene is illuminated with structured light, wherein the unit includes an imaging lens system with longitudinal chromatic aberration arranged between the scene and an imaging sensor;
   depth processing circuitry to generate depth information on the basis of the second images; and
   sharpness processing circuitry to generate an output image based on the depth information and the first images.

2. The imaging system according to claim 1, wherein the optical unit comprises a projector to illuminate the scene with structured light, the projector comprising a controllable projection light source and a projection lens system with longitudinal chromatic aberration arranged between the light source and the scene.

3. The imaging system according to claim 2, wherein optical axes of the light source and the projector are parallel to each other.

4. The imaging system according to claim 1, wherein the sharpness processing circuitry is configured to generate the output image based on the first images after exchanging sharpness information among the first images.

5. The imaging system according to claim 4, wherein the imaging lens system and the projection lens system have the same longitudinal chromatic aberration.

6. The imaging system according to claim 2, wherein the projector comprises an optical element including transparent and at least partially opaque features forming a shadow pattern.

7. The imaging system according to claim 6, wherein the shadow pattern is a greyscale coded pattern.

8. The imaging system according to claim 1, wherein the optical unit is configured to capture the first images and the second images alternately.

9. The imaging system according to claim 1, further comprising
   a light source to illuminate the scene with non-structured light during capturing of the first images.

10. The imaging system according to claim 9, wherein the light source comprises one or more optical fibers with exit faces oriented to the scene and junction faces connectable to an external light source.

11. The imaging system according to claim 9, wherein the light source is configured to illuminate the scene with a broadband emission spectrum covering at least the spectral range of visible light.

12. The imaging system according to claim 9, wherein the light source is configured to illuminate the scene with two or more separated narrowband emission spectra.

13. The imaging system according to claim 1, wherein the depth processing circuitry is configured to generate the depth information from the second images by optical triangulation.

14. The imaging system according to claim 1, wherein the sharpness processing circuitry is configured to obtain spatial frequency distributions of the first images as sharpness information, to extract high frequency components of the spatial frequency distributions from at least one of the first images, to add the extracted high frequency components to the remaining first images to generate corrected first images, and to generate the output image by combining the corrected first images using the depth information.

15. An endoscope system comprising the imaging system according to claim 1.

16. An endoscope comprising:
   a tube portion;
   a tip portion attached at an end face of the tube portion and comprising an optical unit to capture, from a scene, first images of different wavelength ranges when the scene is illuminated with non-structured light and second images of different wavelength ranges when the scene is illuminated with structured light, wherein the optical unit includes an imaging lens system with longitudinal chromatic aberration is arranged between the scene and an imaging sensor;

depth processing circuitry to generate depth information on the basis of the second images; and sharpness processing circuitry to generate an output image base on the depth information and the first images.

17. The endoscope according to claim 16, further comprising a light source to illuminate the scene during capturing of the first images.

18. The endoscope according to claim 16, wherein the optical unit comprises a projector to illuminate the scene with structured light, the projector comprising a controllable projection light source and a projection lens system with longitudinal chromatic aberration arranged between the projection light source and the scene.

19. An imaging method comprising:

capturing, from a scene, first images of different wavelength ranges when the scene is illuminated with non-structured light and second images of different wavelength ranges when the scene is illuminated with structured light, wherein an imaging lens system with longitudinal chromatic aberration is arranged between the scene and an imaging sensor;

generating depth information on the basis of the second images; and generating, by using the depth information, an output image by combining the first images.

20. The imaging method according to claim 19, wherein depth information is generated by using optical triangulation of image portions identified by a shadow pattern of the structured light.

21. An imaging system comprising:

first means arranged in an equipment for capturing, from a scene, first images of different wavelength ranges when the scene is illuminated with not-structured light and second images of different wavelength ranges when the scene is illuminated with structured light, wherein the first and second images are captured by using an imaging lens system with longitudinal chromatic aberration;

second means for generating depth information on the basis of the second images, wherein the second means are connected to the first means in terms of signal transmission, and third means for generating, by using the depth information, an output image by combining the first images, and wherein the third means are connected to the first and second means in terms of signal transmission.

* * * * *